United States Patent [19]

Hearst et al.

[11] 4,124,598
[45] Nov. 7, 1978

[54] PSORALENS

[75] Inventors: John E. Hearst; Henry Rapoport; Stephen Isaacs, all of Berkeley; Che-Kun J. Shen, Albany, all of Calif.

[73] Assignee: Hoffmann-La Roche Inc., Nutley, N.J.

[21] Appl. No.: 734,031

[22] Filed: Oct. 20, 1976

[51] Int. Cl.² ............................................. C07D 493/04
[52] U.S. Cl. .......................... 260/343.21; 260/326 D; 536/22; 424/180
[58] Field of Search ..................... 260/343.2 R, 343.21

[56] References Cited

U.S. PATENT DOCUMENTS 3,201,421  8/1965  Kaufman ....................... 260/343.2 R

OTHER PUBLICATIONS

Musajo et al., Chemical Abst., vol. 79, 1973, 27942b.
Ben-Hur et al., Chem. Abst., vol. 80, 1974 116713r.

*Primary Examiner*—Natalie Trousof
*Assistant Examiner*—Jane T. Fan
*Attorney, Agent, or Firm*—Samuel L. Welt; George M. Gould

[57] ABSTRACT

New psoralen compounds have been synthesized. The compounds all include the addition of substituent groups at the 4' position on the basic trioxsalen structure. Specifically, the compounds have the structure:

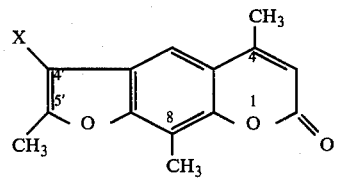

wherein X may be any desired substituent such as halogenated alkyls, alcohols, ethers, aminoalkyls, etc. The new substituted psoralens exhibit high solubility in aqueous solution and low dissociation constants from deoxyribonucleic acid (DNA), as well as a reactivity with ribonucleic acids (RNA). Such psoralen compounds find use in the study of secondary structures of nucleic acids; as inhibitors of RNA replication; in the inactivation of viruses; and in the photo chemotherapy of psoriasis.

5 Claims, 2 Drawing Figures

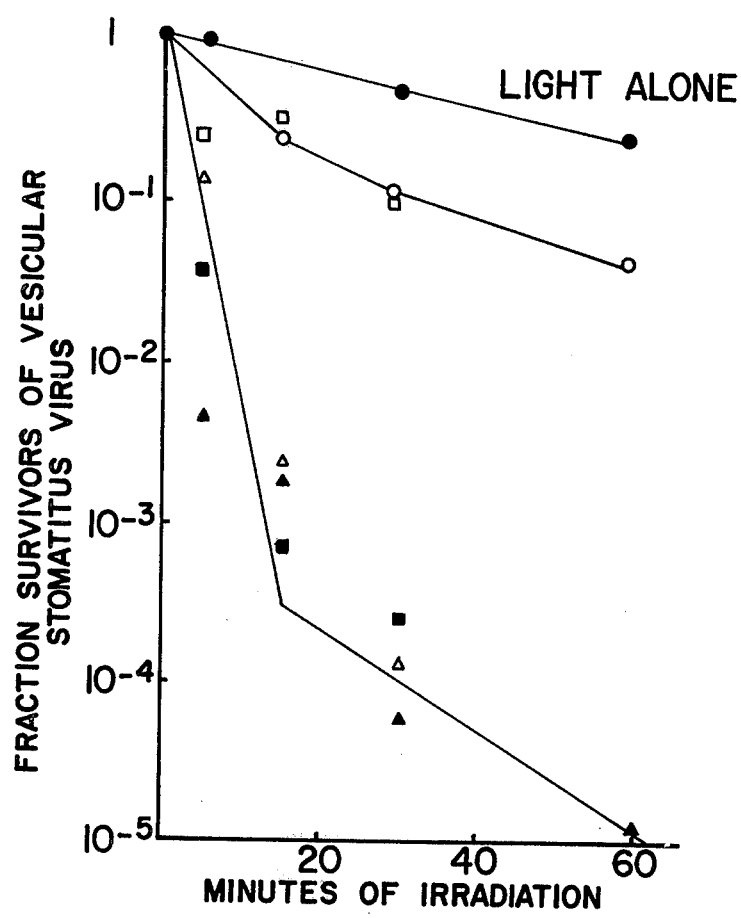
FIG_1
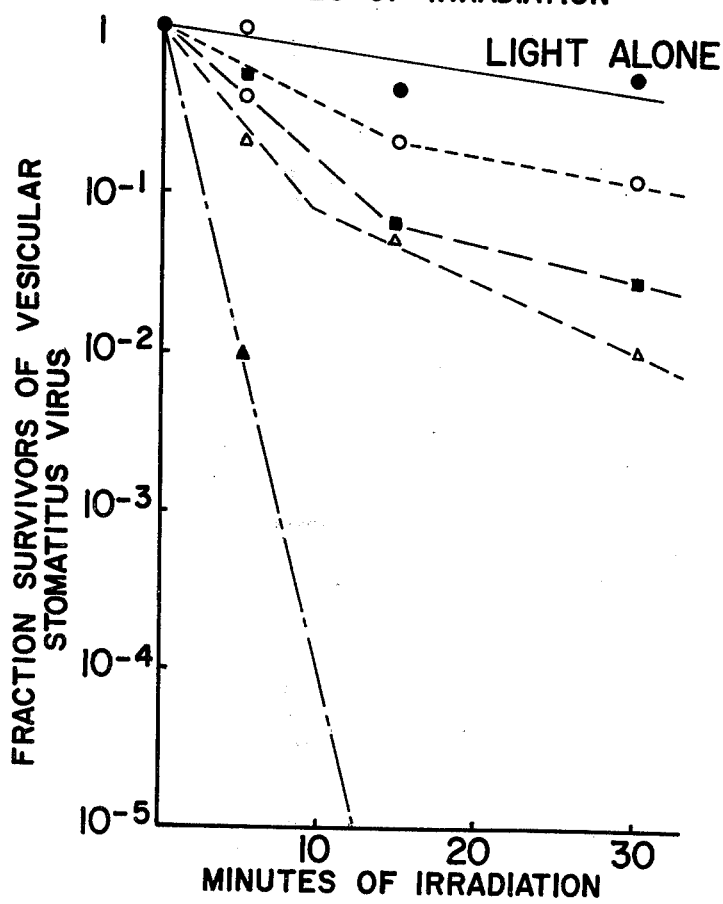
FIG_2

PSORALENS

BACKGROUND OF THE INVENTION

Psoralens are the linear isomers of the furocoumarin family and they occur naturally in certain fruits and seeds, e.g., *Ammi majus* and *Psoralea corylifolia*. Extracts of these fruits and seeds have been used since ancient times as dermal sensitizing agents in the treatment of vitiligo. Topical application of psoralen extracts, followed by irradiation with light, results in a stimulation of melanin production, thus producing a dermal "tanning" effect.

In recent years, psoralens have been utilized in the photo-chemotherapy of psoriasis. In such treatment, psoralens are administered orally or topically to a patient. Subsequently, the skin is exposed to ultra-violet radiation. A high percentage of remissions of the disease occur after such treatment.

With increasing study of, and interest in, molecular biology, the psoralens have been investigated with respect to their ability to form covalent bonds with nucleic acids. Because of their planar structure, psoralens can intercalate between the base pairs in the double helix molecular structure of nucleic acids. Upon irradiation with light of the proper wavelength, the psoralens may form covalent bonds with pyrimidine nucleotides that occur as integral entities of nucleic acid strands. Achieving covalently bonded psoralen bridges or crosslinks between the nucleic acid strands of the double helix presents another tool for use in studying, in vivo, secondary structures of nucleic acids. In addition, the psoralens provide a means for inactivating viruses for the purpose of vaccine production, and also as potential chemotherapeutic agents. The covalently bonded psoralens act as inhibitors of DNA replication and thus have the potential to slow down, or stop the replication process. The covalent bond can only be produced in a two step process by first intercalating the psoralen into the nucleic acid helix, and secondly, by exposing those sites to electromagnetic radiation. Thus, it is immediately apparent that the covalent bonding can be controlled both temporally and spacially.

It will be also apparent that crosslinking can only occur for those psoralen molecules that are present at the right place at the right time, i.e., a psoralen molecule must have intercalated in the correct position at the exact moment radiant energy arrives at that site. The presence of a psoralen molecule at the proper position is dependent upon the solubility of the psoralen in aqueous solution and upon the dissociation constant for the non-covalent binding of the psoralen to nucleic acid. Thus, the higher the solubility, the greater number of molecules in the surrounding liquid medium available to binding sites. Similarly, the lower the dissociation constant, the greater the number of psoralens occupying a potential binding site at any moment in time. The dissociation constant, $K_D$, for non-covalent binding of the psoralen to the nucleic acid is defined by the expression:

$$K_D = (P)(S)/(PS)$$

Where $(P)$ is the concentration of free psoralen, $(S)$ is the concentration of unoccupied binding sites where each base pair on a nucleic acid is considered to be a binding site, and $(PS)$ is the concentration of psoralen-bound sites.

BRIEF DESCRIPTION OF THE INVENTION

The present invention is concerned with improved psoralens exhibiting superiority over prior known psoralens with respect to monoaddition to nucleic acids. Superior, in this sense, refers to the resulting density of covalently bound psoralen on the nucleic acid without replenishment of reagent at a common initial concentration of binding sites and total psoralen concentration.

The improved psoralens have two advantages, i.e., they have improved solubilities in water, and/or they have low dissociation constants from DNA and/or RNA.

More specifically, it has been found that 4'-substituted psoralens possess the desired properties referred to above.

It is therefore an object of the invention to provide improved psoralens that are 4'-adducts of 4,5',8-trimethyl psoralen (trioxsalen).

It is another object of the invention to provide 4'-halogenated alkyl adducts of trioxsalen.

It is another object of the invention to provide 4'-alcohol adducts of trioxsalen.

It is yet another object of the invention to provide 4'-ether adducts of trioxsalen.

It is another object of the invention to provide 4'-aminoalkyl adducts of trioxsalen.

It is still another object of the invention to provide psoralens having high solubility in water.

It is yet another object of the invention to provide psoralens having low dissociation constants from DNA and RNA.

It is another object of the invention to provide psoralens having improved abilities to covalently react with DNA and RNA.

Other objects and advantages of the invention will become apparent from the following description, drawing, and appended claims.

BRIEF DESCRIPTION OF THE INVENTION

The drawing comprises two FIGS. of which:

FIG. 1 is a graphical illustration of the ability of the psoralens of the invention to inactivate an RNA animal virus, vesicular stomatitis virus, at high concentration dosage after different doses of long wavelength UV irradiation. In the graphs, the solid circles (•) = light alone; the open circles (o) = trioxsalen at 10 μg/ml; the open squares (□) = trioxsalen at 30 μg/ml; the solid squares (■) = 4'-hydroxymethyl trioxsalen at 30 μg/ml; the open triangles (Δ) = 4'-trioxsalen at 30 μg/ml; and the solid triangles (▲) = 4'-aminomethyl trioxsalen at 20 μg/ml.

FIG. 2 is a graphical illustration of the ability of the psoralens of the invention to inactivate an RNA animal virus, vesicular stomatitis virus, at low concentration dosage after different doses of long wavelength UV irridiation. In the graphs, the solid circles (•) = light alone; the open circle (o) = trioxsalen at 10 μg/ml; the solid square (■) = 4'-hydroxymethyl trioxsalen at 1 μg/ml; the open triangle (Δ) = 4'-methoxymethyl trioxsalen at 3 μg/ml; and the solid triangle (▲) = 4'-aminomethyl trioxsalen at 2 μg/ml.

DETAILED DESCRIPTION OF THE INVENTION

The basic psoralen structure is:

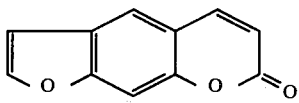

while the two most widely known and widely used derivatives are 8-methoxy psoralen (commonly called — methoxsalen):

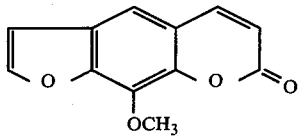

and 4,5',8-trimethyl psoralen (commonly called — trioxsalen):

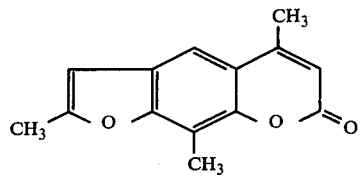

The new psoralens of the invention are all derivatives of trioxsalen in that they are 4'-adducts of trioxsalen. All of the new psoralens have various functional groups, e.g., halogenated alkyls, alcohols, ethers, aminoalkyls, particularly, halogenated lower alkyls, hydroxy lower alkyls, lower alkoxy lower alkyls and primary amino lower alkyls, substituted into the trioxsalen molecule on the 4' carbon atom.

Specific examples of the new psoralens are 4'-chloromethyl-4,5',8-trimethyl psoralen:

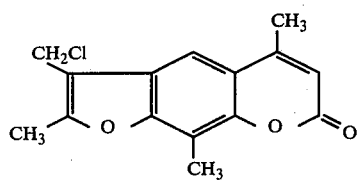

4'-hydroxymethyl-4,5',8-trimethyl psoralen:

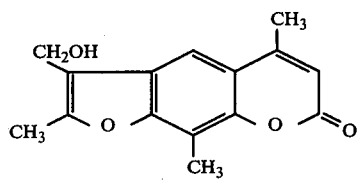

4'-methoxymethyl-4,5',8-trimethyl psoralen

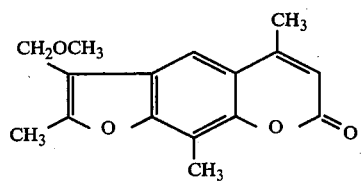

4'-N-Phthalimidomethyl-4,5',8-trimethyl psoralen:

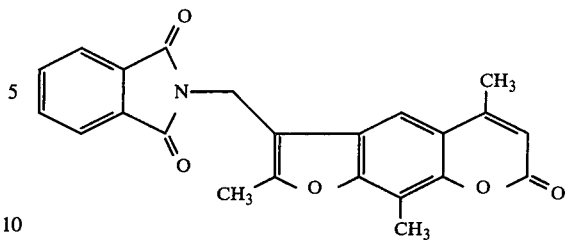

and, 4'-aminomethyl-4,5',8-trimethyl psoralen hydrochloride:

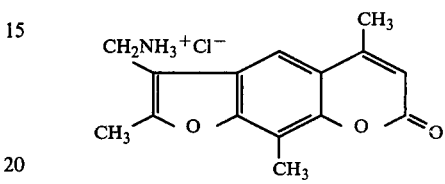

The psoralens, 4'-chloromethyl-4,5',8-trimethyl psoralen and N-(4'-methyl-4,5',8-trimethyl psoralen) phthalimide find use as intermediates in the production of the remaining psoralens of the invention. There is some evidence that these psoralens may have some use in the same areas as the other psoralens. In the case of the 4'-chloromethyl psoralen, the chloromethylsubstituent is readily hydrolysed in aqueous solution and it is therefore difficult to ascertain its specific activity with respect to DNA or RNA bonding. In any event, the role of both compounds will become apparent from the description hereinafter.

The psoralens, 4'-hydroxymethyl-4,5',8-trimethyl psoralen; 4'-methoxymethyl-4,5',8-trimethyl psoralen; and 4'-aminomethyl-4,5',8-trimethyl psoralen, all exhibit excellent reactivity with DNA, as will be hereinafter noted.

Synthesis of the psoralens

As a matter of convenience, all the psoralens of the invention can be synthesized from 4,5',8-trimethyl psoralen (trioxsalen). Trioxsalen is a commercially available (e.g., Paul B. Elder Co.,) psoralen, so it is readily accessible. Although the methods described herein all start with trioxsalen, it will be apparent that other known synthesis methods may be utilized.

For convenience, all syntheses are presented as specific examples, but it should be understood that larger or smaller quantities may be produced in accordance with the methods set forth. Also, variations in the methods set forth will be apparent to those skilled in the art.

EXAMPLE I

4'-chloromethyl-4,5',8-trimethyl psoralen

Trioxsalen (659 mg, 2.89 m mole) was dissolved in 75 ml glacial acetic acid by gentle heating and cooled to room temperature. 5 ml of chloromethyl-methyl ether was added and the mixture set aside for 24 hours, followed by a second 5 ml addition of the ether. After 48 hours, the reaction flask was placed on ice and 12 hours later an abundant white precipitate was collected. Recrystallization from acetonitrile gave 435 mg pure product. Another crop was isolated from the filtrate to give 499 mg total product. (yield 62.5%). Analysis of the product produced the following data:

mp 215°–17°; NMR (CDCl$_3$) δ2.6–2.7 (9 H, m) 4.8 (2 H, s) 6.3 (1 H, s), 7.6 (1 H, s; mass spectrum m/e (relative intensity) 276 (m+, 48), 278 (m + 2, 15).

ANALYSIS: Calculated for C$_{15}$H$_{13}$Cl O$_3$: C, 65.1 H, 4.7; Cl, 12.8. Found: C, 65.0; H, 4.8; Cl, 12.6.

EXAMPLE II

4'-hydroxymethyl-4,5',8-trimethyl psoralen

4'-chloromethyl-4,5',8-trimethyl psoralen (53 mg, 0.192 m mole) from the previous synthesis was refluxed in 50 ml distilled water for 7 hours followed by cooling on ice for 2 hours. The product was separated and collected by filtration and then dried to yield 25 mg of product. The percentage yield was 50.5. Analysis of the product gave the following:

mp 221°–24°; NMR (DMSO-d$_6$) δ2.5–2.7 (9 H, m). 4.5–4.7 (2 H, m) 5.0–5.2 (1 H, bs), 6.3 (1 H, s), 7.8 (1 H, s) mass spectrum m/e (relative intensity) 258 (M+, 100) 241 (17).

ANALYSIS: Calculated for C$_{15}$H$_{14}$O$_4$: C, 69.8; H, 5.4. Found: C, 69.5; H, 5.5

EXAMPLE III

4'-methoxymethyl-4,5',8-trimethyl psoralen

4'-chloromethyl-4,5',8-trimethyl psoralen (78 mg, 0.28 m mole) was refluxed in 30 ml methanol for 5 hours. Removal of the solvent by evaporation gave 74 mg of the product. Yield was 97.2%. Analysis of the product indicated:

mp 171°–174°; NMR (CDCl$_3$) δ2.4–2.6 (9 H, m) 3.4 (3 H, s), 4.6 (2 H, s) 6.3 (1 H, s): mass spectrum m/e (relative intensity) 272 (M+, 93), 241 (100).

ANALYSIS: Calculated for C$_{16}$H$_{16}$O$_4$: C, 70.6; H, 5.9. Found: C, 70.4; H, 5.9.

EXAMPLE IV

4'-N-Phthalimidomethyl-4,5',8-trimethyl psoralen

4'-chloromethyl-4,5',8-trimethyl psoralen (200 mg, 0.73 m mole) as obtained in Example I, potassium phthalimide (165 mg. 0.89 m mole, purified by refluxing 2 hours in acetone), and 20 ml N, N'-dimethyl formamide were heated to 100° for 6 hours with constant stirring. The solvent was evaporated in vacuo heating in a water bath leaving behind a yellow paste which was taken up in chloroform and washed 3 times with water. The chloroform-psoralen was dried over MgSO$_4$ and then filtered and evaporated to yield 222 mg (79.3%) of product. Analysis of the product indicated:

mp 267°–274°: NMR (CDCl$_3$) δ 2.5–2.8 (9 H, m), 5.0 (2 H, s), 6.3 (1 H, s), 7.7–7.8 (7 H, d), 8.0 (1 H, s), mass spectrum m/e (relative intensity) 387 (m+, 80), 241 (20), 240 (75).

EXAMPLE V

4'-aminomethyl-4,5',8-trimethyl psoralen hydrochloride

4'-N-phthalimidomethyl-4,5',8-trimethyl psoralen (VII, 848 mg, 2.2 mM), hydrazine hydrate (85% in water, 0.5 ml) and 95% ethanol (100 ml) were refluxed for 4 hours followed by a second 0.5 ml addition of the hydrazine-hydrate solution. After extending the reflux 2 hours no starting material remained as determined by TLC (diethyl ether). The ethanol was evaporated and the residue taken up in 200 ml 0.1N NaOH followed by extraction with three 50 ml portions of chloroform to yield 193 mg (34%) of the crude amine. To prepare the hydrochloride, the amine was taken up in 100 ml 1.2N HCl which was extracted with three 30 ml portions of chloroform to remove impurities. Evaporation in vacuo of the acidic solution gave the crude hydrochloride which was dissolved in 175 ml abs. ETOH and precipitated by the addition of an equal volume of diethyl ether. After cooling over night (7°), 161 mg of pure product was collected; mp 260°–269°; NMR (CDCl) as the amine δ 1.4–1.6 (2 H, s), 2.6–2.7 (9 H, m), 4.1 (2 H, s), 6.3 (1 H, s), 7.7 (1 H, s); mass spectrum m/e (relative abundance) 257 (M+, 36), 240 (100).

ANALYSIS: Calculated for C$_{15}$H$_{16}$ClNO$_3$: C, 61.3: H, 5.5; N, 4.8, Cl 12.1. Found: C, 61.0; H, 5.5; N, 4.7; Cl 11.9.

Adducts related to those already specifically disclosed above may be prepared utilizing the same preparation procedures. For purposes of the invention, however, the important properties of such adducts are high solubility in aqueous solution, and a low dissociation constant from DNA and/or RNA.

In order to study solubilities and dissociation constants, it is most convenient to prepare tritiated derivatives of the psoralen compounds. Thus, well-known radiation counting methods may be utilized to monitor the presence of the psoralens in solutions, or in nucleic acids.

The tritium labeled psoralens are prepared from trioxsalen having tritium incorporated therein. Specifically, tritiated water is refluxed with normal trioxsalen to effect an exchange of tritium with the hydrogen on the trioxsalen. The tritiated trioxsalen is recovered and utilized to prepare the psoralens of the invention according to the examples previously set forth.

The following example presents a specific method for preparing the tritiated trioxsalen:

EXAMPLE VI

Tritiated 4,5',8-trimethyl psoralen 4,5',8-trimethyl psoralen (1153 mg) T$_2$O (aqueous, 100 curies in 4 ml), dioxane (67.5 ml) and fuming H$_2$SO$_4$ (30% SO$_3$, 7.5 ml) were refluxed for 2 hours with constant stirring followed by cooling to room temperature. 125 ml ice water was added and the mixture cooled on ice for 1 hour. The precipitate was collected by filtration and air dried to give 900 mg (78%) crude product. Mass spectrum analysis indicated m/e (relative abundance) 228 (m+, 100). A small amount of the material (30 mg) was dissolved in 75 ml 100% ETOH and about 2 gm charcoal added. The mixture was refluxed for 10 minutes, then immediately filtered (hot) through a fine sintered glass filter to remove the charcoal. The filtrate was evaporated and the residue recrystallized from methanol/water (about 90:10). Analytical TLC of the product (CHCl$_3$/CH$_3$OH$_2$98:2) found more than 95% of the counts in the trimethyl psoralen. The specific activity of the compound was determined by counting aliquots of an absolute ethanol solution of known concentration in toluene-omnifluor. The specific activity was found to be 6.7 × 10$^5$ cpm.

Quantities of the psoralens of the invention were prepared as per Examples I to V to yield tritiated products.

The tritiated psoralens were then utilized to study their binding efficiencies with nucleic acid. The studies were directed to securing data on the solubilities and the dissociation constants from both DNA and RNA. In addition, the psoralens' ability to covalently bind with DNA and RNA was also studied.

The studies and results thereof were as follows:

In order to establish the dissociation constants from DNA and RNA, the non-covalent binding was ascertained. Non-covalent binding determines the presence of the psoralen within the nucleic acid helix. Its presence is determined in the absence of any radiant energy. As noted before, radiant energy is necessary to activate the psoralen covalent binding reaction with nucleic acid base pairs.

To determine the non-covalent binding, Calf thymus DNA (Sigma Type I) was dissolved in a 0.01 M Tris 0.001 M EDTA pH 8.5 buffer at a concentration of 25 ug/ml. A quantity of this DNA solution was placed in a dialysis bag (pretreated by boiling in NaHCO$_3$), and the various tritiated derivatives were added inside the bag in half the cases and outside the bag in the other half. The molar ratio of psoralen molecules to base pairs was approximately 1:25. The bags were placed in vials filled with 18 ml of buffer and put on a shaker for 48–60 hours. After this period, radioactivity was determined both inside and outside the bags and the optical density of the DNA solution measured. From this information, and the specific activity of each derivative, the amount of drug non-covalently bound to the DNA was determined. Binding of the derivatives to Drosophila melanogaster ribosomal RNA was measured in exactly the same manner.

The results of the equilibrium dialysis measurements are presented in Table 1 below. The units of the dissociation constants are moles/liter. Solubilities and molar extinction coefficients ($\epsilon$) were obtained in pure water, the equilibrium constants ($K_D$) in 0.01 M Tris.

one psoralen for every three base pairs. The irradiation was carried out in one of the two following devices.

The low intensity irradiations were performed with a modified slide projector which was fitted with a 400 watt General Electric mercury vapor lamp (H 400 A 33-1/T16). The image of the arc was focused on the same cell, jacketed by a cobaltous nitrate solution which was also used for the high intensity irradiations. The light intensity delivered to the sample in this device was 4 to 6 mw/cm$^2$. The high intensity irradiations were carried out in a device containing two of the sam 400 watt General Electric mercury vapor lamps which were mounted on either side of a double walled sample chamber at a distance between centers of 4.0 cm. The chamber was cooled to 10° C. by continuous circulation of a temperature regulated solution of cobaltous nitrate (40% w/w). The cobalt solution served as an ultraviolet filter which allowed a maximum transmittance of 365 nm light and a window from approximately 340–380 nm. The intensity of the light at the surface of the inner sample chamber was approximately 100 mw/cm$^2$. The nucleic acid-psoralen mixture was placed in the inner chamber where it was continuously stirred throughout the irradiation. Aliquots of each solution (derivative plus nucleic acid) were taken at 20, 40 and 60 minutes. Each aliquot was then extracted twice with chloroform/iso-amyl alcohol (24:1) to remove unreacted psoralen followed by exhaustive dialysis against 0.01 M Tris, 0.001 M EDTA buffer. The successful extraction of unbound psoralen by the chloroform-isoamyl alcohol required the aqueous phase to be at least 0.15 M in

TABLE I

The Extinction Coefficients, Solubilities, Dissociation Constants, and Ratios of Concentrations of Occupied to Unoccupied Binding Sites in Saturated Solutions for Psoralen Derivatives.

| 1. Compounds | 2. 250 nm $l^\epsilon$/mole cm | 3. Solubility μg/ml | 3. Solubility mole/l | 4. $K_D$DNA mole/l | 5. Column 3/Column 4 (PS)/(S) for DNA in Saturated Solution | 6. $K_D$RNA mole/l | 7. Column 3/Column 6 (PS)/(S) for RNA in Saturated Solution |
|---|---|---|---|---|---|---|---|
| 8-methoxypsoralen | $1.9 \times 10^4$ | 36 | $1.7 \times 10^{-4}$ | $2.5 \times 10^{-3}$ | 0.068 | $1.7 \times 10^{-2}$ | 0.010 |
| 4,5′,8-trimethylpsoralen | $1.8 \times 10^4$ | 0.6 | $2.6 \times 10^{-6}$ | $5.6 \times 10^{-5}$ | 0.046 | $10^{-4}$ | 0.026 |
| 4′-methoxymethyl-4,5′,8-trimethyl psoralen | $2.1 \times 10^4$ | 10 | $3.7 \times 10^{-5}$ | $9.4 \times 10^{-5}$ | 0.39 | $10^{-3}$ | 0.037 |
| 4′-hydroxymethyl-4,5′,8-trimethyl psoralen | $2.5 \times 10^4$ | 41 | $1.6 \times 10^{-4}$ | $2.9 \times 10^{-4}$ | 0.55 | $10^{-3}$ | 0.16 |
| 4′-aminomethyl-4,5′,8-trimethyl-psoralen hydrochloride | $2.5 \times 10^4$ | $10^4$ | $3.4 \times 10^{-2}$ | $6.6 \times 10^{-6}$ | 5000 | $2 \times 10^{-5}$ | 1700 |

The data in Table I for 8-methoxypsoralen in columns two through seven were calculated from results presented in the literature. All other data results from work by the inventors.

8-methoxypsoralen and 4,5′,8-trimethylpsoralen are included in Table I as comparisons with the psoralens of the invention.

The covalent binding of the psoralens to DNA and RNA was studied. To achieve covalent binding, it is necessary to supply radiant energy (light) to the binding sites. These studies were carried out as follows:

The DNA and RNA used in the covalent binding studies have been described previously. Samples of each nucleic acid were prepared at a concentration of 25 ug/ml in 0.01 m Tris 0.001 M EDTA buffer. The radioactive-psoralen derivatives were added in a ratio of NaCl. Finally, the optical density of the nucleic-acid psoralen mixture was taken and its radioactivity determined, thus giving the amount of derivative covalently bound to the DNA or RNA. Taking samples, at spaced time intervals also permitted an assessment of the kinetics of the covalent binding.

Table II below presents the results of these studies with respect to DNA:

Table II

Low Intensity Photoaddition of Psoralen Derivatives in a Solution Containing 25 μg/ml DNA and a Psoralen to Base Pair Molar Ratio of 1:3.

| Time of irradiation (min.) | trioxsalen A[1] | trioxsalen B[2] | 4′-hydroxymethyl trioxsalen A | 4′-hydroxymethyl trioxsalen B | 4′-aminomethyl trioxsalen hydrochloride A | 4′-aminomethyl trioxsalen hydrochloride B |
|---|---|---|---|---|---|---|
| 5 | 19.7 | 15.5 | 89.0 | 3.0 | 15.0 | 19.3 |
| 10 | 15.5 | 19.7 | 59.6 | 4.6 | 10.5 | 27.4 |

Table II-continued

Low Intensity Photoaddition of Psoralen Derivatives in a Solution Containing 25 μg/ml DNA and a Psoralen to Base Pair Molar Ratio of 1:3.

| Time of irradiation (min.) | trioxsalen A[1] | B[2] | 4'-hydroxymethyl trioxsalen A | B | 4'-aminomethyl trioxsalen hydrochloride A | B |
|---|---|---|---|---|---|---|
| 30 | 13.7 | 22.1 | 26.0 | 10.3 | 6.9 | 41.8 |
| 60 | 12.8 | 23.6 | 19.5 | 13.8 | 5.9 | 48.7 |
| 90 | 10.6 | 28.5 | 17.2 | 15.7 | 5.5 | 52.4 |

[1] $A = \frac{\text{moles of base pairs}}{\text{moles of bound psoralen}}$

[2] B = percent of added psoralen covalently bound

From the data presented in Table II, it is apparent that 4'-aminomethyl trioxsalen reacts with DNA much faster than trioxsalen which in turn has a greater initial rate of photochemical binding than 4'-hydroxymethyl trioxsalen. At an irradiation time of 90 minutes, the moles of psoralen bound per mole of base pairs are 0.18 for the aminomethyl compound, while that of trioxsalen and the hydroxymethyl compound are 0.09 and 0.06, respectively. Table II also shows that after 90 minutes of irradiation, over half of the molecules of 4'-aminomethyl trioxsalen in the solution are covalently bound to DNA while more than 80% of 4'-hydroxymethyl trioxsalen remains free in the solution. These differences most likely result from the influence of the molecular structures of the different psoralens on their solubilities, on their photochemical reactivities, and on the photodestruction of the compounds themselves.

Table III below presents the results of high intensity radiation on the covalent binding of the psoralens to DNA:

Table III

High Intensity Photoaddition of Psoralen Derivatives in a Solution Containing 25 μg/ml DNA and a Psoralen to Base Pair Ratio of 1:3.

| Time of irradiation (mins.) | trioxsalen A | B | 4'-hydromethyl trioxsalen A | B | 4'-methoxymethyl trioxsalen A | B | 4'-aminomethyl trioxsalen hydrochloride A | B |
|---|---|---|---|---|---|---|---|---|
| 20 | 11.6 | 25.9 | 9.1 | 33.0 | 14.1 | 21.3 | 4.7 | 63.8 |
| 40 | 10.6 | 28.3 | 9.2 | 32.6 | 14.3 | 21.0 | 4.8 | 62.5 |
| 60 | 12.2 | 24.6 | 9.1 | 33.0 | 13.8 | 21.7 | 4.8 | 62.5 |

[1] $A = \frac{\text{moles of base pairs}}{\text{moles of covalently bound psoralen}}$

[2] B = percent of added psoralen covalently bound.

Table IV presents the results of high intensity irradiation in achieving covalent binding of the psoralens with RNA:

Table IV

High Intensity Photoaddition of Psoralen Derivatives in a Solution Containing 25 μg/ml RNA and a Psoralen to Base Pair Ratio of 1:3.

| Time of irradiation (mins.) | trioxsalen A | B | 4'-hydromethyl trioxsalen A | B | 4'-methoxymethyl trioxsalen A | B | 4'-aminomethyl trioxsalen hydrochloride A | B |
|---|---|---|---|---|---|---|---|---|
| 20 | 23.1 | 13.0 | 26.3 | 11.5 | 264.2 | 1.2 | 5.1 | 59.4 |
| 40 | 21.6 | 13.9 | 24.8 | 12.1 | 216.8 | 1.4 | 5.3 | 57.2 |
| 60 | 20.6 | 14.8 | 23.5 | 13.0 | 183.4 | 1.6 | 5.3 | 57.3 |

[1] $A = \frac{\text{moles of base pairs}}{\text{moles of covalently bound psoralen}}$

[2] B = percent of added psoralen covalently bound.

From the data presented in Tables I, II, III and IV above, the following conclusions can be drawn:

Table I presenting th dissociation constants for equilibrium binding to DNA, indicates that 4'-aminomethyl-4,5',8trimethyl psoralen binds about 8 times more strongly to DNA than does trioxsalen. The binding of trioxsalen is 5 times stronger than 4'-hydroxymethyl and 2 times stronger than 4'-methoxymethyl trioxsalen. These two new derivatives still, however, bind 10 times more strongly to DNA than methoxsalen the other common commerically available psoralen.

Further studies have shown the relative solubilities of the psoralens to be in the order 4'-aminomethyl trioxsalen, 4'-hydroxymethyl trioxsalen, 4'-methoxymethyl trioxsalen, methoxsalen, and trioxsalen are approximately 10,000:68:17:80:1. By dividing the molar solubility by the dissociation constant, it is shown that at equilibrium in a solution saturated with the respective psoralen, it is not possible to saturate the DNA binding sites with either trioxsalen or methoxsalen. The best one can do is approxiamtely one psoralen per 20 base pairs. Column 5 in Table I shows the ratio of bound to free sites in a DNA solution saturated with the appropriate psoralen. The 4'-hydroxmethyl trioxsalen and 4'-methoxymethyl trioxsalen can be expected to nearly achieve saturation of DNA sites by binding one psoralen per three base pairs [(PS)/(S) = 0.5] while the 4'-aminoethyl trioxsalen is calculated to be $10^4$ times more effective at reaching this state of site saturation (it is 150 times more soluble than 4'-hydroxymethyl trioxsalen, and binds about 100 times more strongly).

The psoralens of the invention are also useful in the inactivation of RNA virus. In this regard, they have an activity that is significantly higher than any other known psoralens. At high dose rates, e.g., 30 μg/ml, 4'-hydroxymethyl-4,5',8-trimethyl psoralen, 4'-methoxymethyl-4,5',8-trimethyl psoralen, and 4'-aminomethyl-4,5',8-trimethyl psoralen, are all nearly one thousand times more effective than the common commercially available 4,5',8-trimethyl psoralen in the inactivation of the RNA animal virus, vesicular stomatitis virus.

This outstanding effectiveness is illustrated in FIG. 1 of the drawing, wherein the curves indicate the survival of plaque forming units of vesicular stomatitus virus as a function of long wavelength UV irradiation times in the presence of the indicated psoralens. At the dose rates illustrated (about 20–30 μg/ml), the vast superiority of the psoralens of the invention over trioxsalen is immediately apparent. All three psoralens of the invention are essentially equivalent of these high dosages. Their equivalence at these high dosages is essentially predictable from their dissociation constants, $K_D$, set forth in Table I herein above; and from their high aqueous solubilities, previously referred to (in the case of 4'-methoxymethyl trioxsalen the solution in supersaturated). At the dosage rates illustrated, the RNA is nearly saturated with non-covalently bound intercalated psoralens. Thus, all three psoralens appear to be equivalent in activity. However, the trioxsalen is only soluble to the extent of 0.6 μg/ml and therefore increasing its concentration from 10 μg/ml (the o points) to 30 μg/ml (the points) has no effect on its ability to inactivate the virus.

FIG. 2 of the drawing presents similar curves to those of FIG. 1, but the data result from much lower concentrations of the psoralens, i.e., 1–3 μg/ml. FIG. 2 also illustrates the undisputed superiority of 4'-aminomethyl-4,5',8-trimethyl psoralen over all the other psoralens, both those of the invention, and the commercial psoralen, trioxsalen. This superiority of the 4'-aminomethyl derivative results from its stronger binding to nucleic acids as is also apparent from reference to the dissociation constants, $K_D$, set forth in Table I.

The data presented in both FIG. 1 and FIG. 2 was secured using the following procedures:

500 μl of phosphate buffered saline containing 5 × $10^4$ virus plaque forming units were added to Petri dishes of 3.5 cm diameter and irradiated in the presence or absence of the psoralen using a type A405 long wavelength UV lamp, P. W. Allen Co., London.

At various time intervals, 50 μl aliquots were sampled from the dishes and the amount of virus plaque forming units was titrated. Dilutions of the aliquot were prepared with adjustable pipettes and plated on monolayers of primary chicken fibroblasts grown in plastic trays. After virus adsorption, the cultures were overlaid with nutrient medium containing 20 percent calf serum and 3% methylcellulose. Neutral red was added after 2 to 4 days incubation at 35° C. The virus was *Vesicular stomatitis* virus Indiana strain.

What is claimed is:

1. A 4,5',8-trimethyl psoralen having an organic functional substituent on the 4' carbon atom said substituent being selected from the group consisting of halogenated lower alkyl, hydroxy lower alkyl, lower alkoxy lower alkyl and primary amino lower alkyl.

2. The compound 4'-chloromethyl-4,5',8-trimethyl psoralen.

3. The compound 4'-hydroxymethyl-4,5',8-trimethyl psoralen.

4. The compound 4'-methoxymethyl-4,5',8-trimethyl psoralen.

5. The compound 4'-aminomethyl-4,5',8-trimethyl psoralen hydrochloride.

* * * * *

UNITED STATES PATENT AND TRADEMARK OFFICE
CERTIFICATE OF CORRECTION

PATENT NO. : 4,124,598

DATED : November 7, 1978

INVENTOR(S) : John E. Hearst et al.

It is certified that error appears in the above-identified patent and that said Letters Patent are hereby corrected as shown below:

Cover Page, line [73]  Assignee; "Hoffmann-La Roche Inc., Nutley, N.J."

should be :

The Regents of the University of California, Berkeley, California

Signed and Sealed this

Fifth Day of June 1979

[SEAL]

Attest:

RUTH C. MASON
*Attesting Officer*

DONALD W. BANNER
*Commissioner of Patents and Trademarks*